United States Patent [19]
Daoud et al.

[11] Patent Number: 6,142,971
[45] Date of Patent: *Nov. 7, 2000

[54] SYSTEM AND METHOD FOR HIGH PRESSURE DELIVERY OF GAS-SUPERSATURATED FLUIDS

[75] Inventors: Adib G. Daoud, San Diego; James M. Gessert, Santa Ana, both of Calif.

[73] Assignee: Therox, Inc., Irvine, Calif.

[*] Notice: This patent is subject to a terminal disclaimer.

[21] Appl. No.: 09/133,984

[22] Filed: Aug. 13, 1998

Related U.S. Application Data

[63] Continuation of application No. 08/915,531, Aug. 15, 1997, Pat. No. 5,893,838.

[51] Int. Cl.[7] .................................................. A61M 37/00
[52] U.S. Cl. ............................ 604/23; 604/26; 604/151
[58] Field of Search ............................... 604/23–26, 131, 604/151, 152, 264, 21, 28, 500

[56] References Cited

U.S. PATENT DOCUMENTS 5,893,838  4/1999  Daoud et al. ............................ 604/26

Primary Examiner—John D. Yasko
Attorney, Agent, or Firm—Fletcher, Yoder & Van Someren

[57] ABSTRACT

A system and method for generating a gas-supersaturated fluid and delivering the fluid at high delivery pressures to thereby prevent bubble nucleation is disclosed. The system comprises a housing for containing a removable fluid assembly for housing a fluid to be gas-supersaturated and a drive assembly for delivering the fluid to a delivery site. The housing assembly comprises a cylinder and a piston which may be advanced along the inner surface of the cylinder to pressurize and to deliver the fluid. To generate a gas-supersaturated fluid, the housing assembly is removed from the system housing, filled with a fluid, and gas is introduced at or slightly above the desired gas partial pressure into the cylinder. To deliver the gas-supersaturated fluid, the fluid assembly is returned to the system housing and the drive assembly advances the piston to increase the hydrostatic pressure to the desired delivery pressure and, after opening a valve, to deliver the gas-supersaturated fluid at the desired high delivery pressure to a delivery site.

37 Claims, 7 Drawing Sheets

SYSTEM AND METHOD FOR HIGH PRESSURE DELIVERY OF GAS-SUPERSATURATED FLUIDS

This application is a continuation of application Ser. No. 08/915,531, filed Aug. 15, 1997, now U.S. Pat. No. 5,893,838.

FIELD OF THE INVENTION

The present invention generally relates to a system and method for the generation and delivery of high pressure gas-supersaturated fluids. More specifically, the present invention relates to a system and method for generating a gas-supersaturated fluid and delivering the fluid at high pressures without bubble formation.

BACKGROUND OF THE INVENTION

Prior art infusion devices have been developed for drug delivery, angiographic dye injection and precision fluid infusion. In general, such infusion devices only support small delivery volumes (approximately 60 cc) at low (for example, less than 20 psi) to medium (for example, up to 1000 psi) delivery pressures.

A system and method capable of delivering a large volume of fluid at an accurate delivery rate may be desirable, for example, for enriching blood with an oxygen-supersaturated solution to provide regional or systemic support to a patient. Another application of oxygen supersaturated fluid would be delivery downstream of a balloon angioplasty site, such as by perfusion guidewire, to reduce or prevent localized ischemia. For delivery and infusion of gas-supersaturated fluids, such as an oxygen supersaturated solution, a high delivery pressure (for example, 4,000 psi) may be desirable to prevent bubble nucleation or formation. An example of a system for delivering gas supersaturated fluids without bubble formation is disclosed in U.S. Pat. No. 5,599,296. When fluid is delivered at high pressures, it is also desirable to provide a safety mechanism for terminating fluid delivery when the delivery pressure exceeds a predetermined limit.

In order to deliver the fluid at a desired volume delivery rate and/or to deliver a desired total volume of the fluid, it is also desirable to provide accurate control of the delivery rate and thus accurate control of the total fluid volume delivered.

In spite of recent advances in the art, for example the above-mentioned U.S. Pat. No. 5,599,296, there remains a need in the art for a fluid delivery system and method for generating and accurately delivering a large volume of gas-supersaturated fluid. There remains a further need in the art for a system capable of generation and delivery of gas-supersaturated fluid at high delivery pressures in order to prevent or minimize bubble nucleation and formation upon infusion into a patient. There remains yet a further need in the art for a fluid delivery system and method for providing a safety mechanism to protect patients and operators by interalia, terminating the fluid delivery if the delivery pressure exceeds a predetermined limit. There remains yet a further need in the art for a fluid delivery system and method for accurate control of the delivery rate and pressure and thus accurate control of the total fluid volume delivered.

SUMMARY OF THE INVENTION

Preferred embodiments of the present invention meet the foregoing needs by providing a system and method for generating a large volume of gas-supersaturated fluid and delivering the fluid to a fluid delivery device at specified fluid delivery rates and at high delivery pressures to prevent bubble nucleation.

The fluid delivery system of the present invention comprises a system housing for containing a removable fluid housing assembly and a drive mechanism assembly. The removable fluid housing assembly comprises a cylindrical fluid housing and a piston which travels along the inner surface of the fluid housing.

The fluid housing assembly is first removed from the system housing and filled with a fluid. The fluid in the fluid housing assembly is supersaturated by introducing a gas at or slightly above the desired gas partial pressure of the fluid. The fluid housing assembly is then returned to the system housing and the drive mechanism assembly advances the piston to increase the hydrostatic pressure of the fluid within the fluid housing until the desired delivery pressure is obtained.

Use of the fluid housing for both generating and delivering the gas-supersaturated fluid simplifies the system configuration by eliminating additional components and also simplifies the method for generating and delivering the gas-supersaturated fluid by eliminating the step of transporting the fluid from one fluid housing to another. Generating and delivering the gas-supersaturated fluid in a single fluid housing also greatly minimizes the issues of corrosion of the fluid housing, contamination of the fluid and bubble nucleation in the fluid.

After the hydrostatic pressure of the fluid within the fluid housing reaches the desired delivery pressure, the gas-supersaturated fluid is delivered through a fluid output tubing for delivery of the fluid to a desired delivery site. For fluid delivery to a patient, for example, a hollow perfusion guide wire or other appropriate delivery device is connected to one end of the fluid output tubing. The fluid delivery rate is controlled and can range from 1 ml/hr to greater than 3,000 ml/hr.

The system of the present invention provides a compact system for generation and delivery of gas-supersaturated solutions in a configuration and size very similar to conventional infusion pumps.

DETAILED DESCRIPTION OF THE INVENTION

Figure 1:
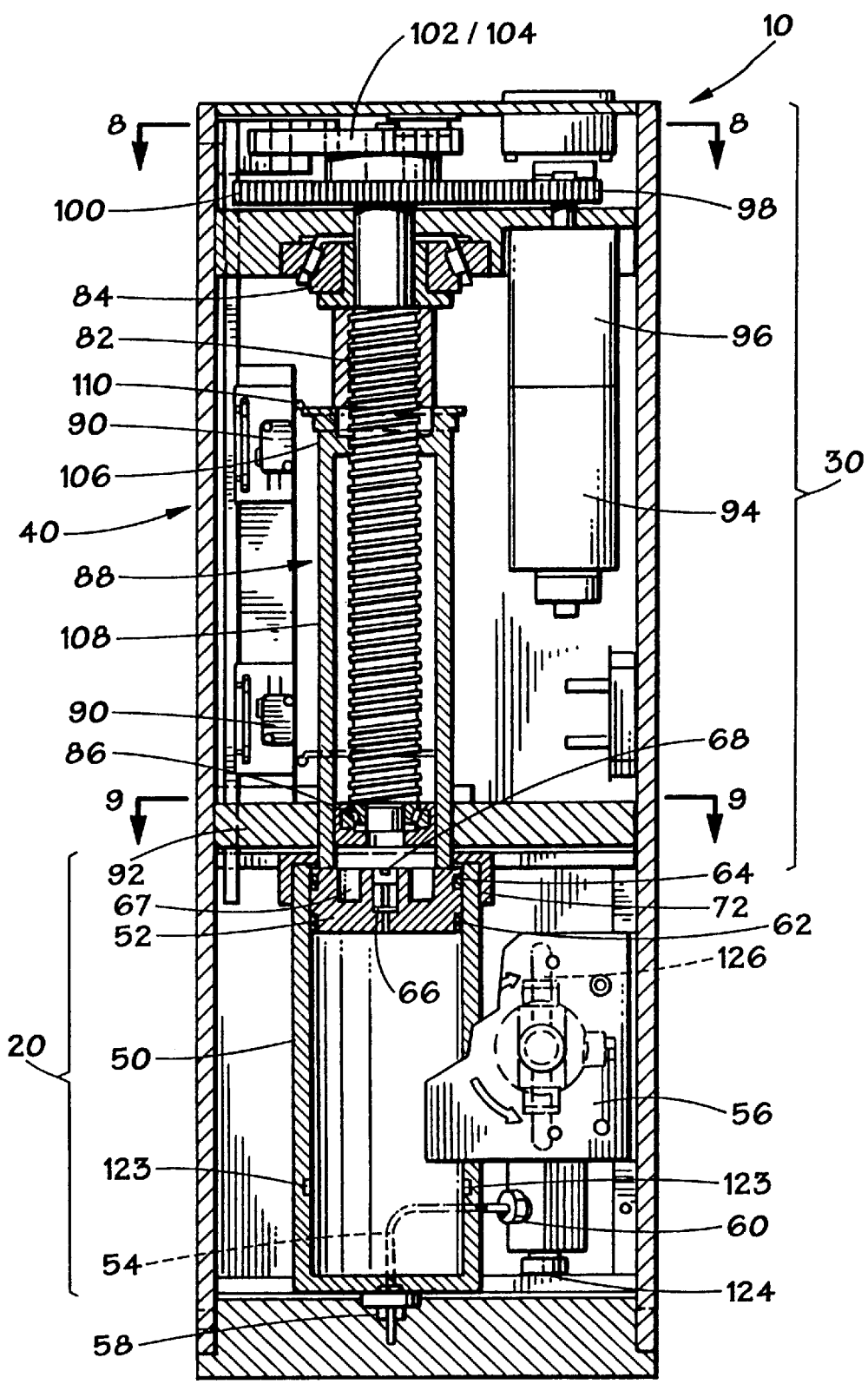
FIG. 1 is a partial cross-sectional front view of a high pressure infusion system of the present invention.

The structure and function of the preferred embodiments can be best understood by reference to the drawings. Where the same reference numerals appear in multiple figures, the numerals refer to the same or corresponding structure in those figures.

Figure 2:
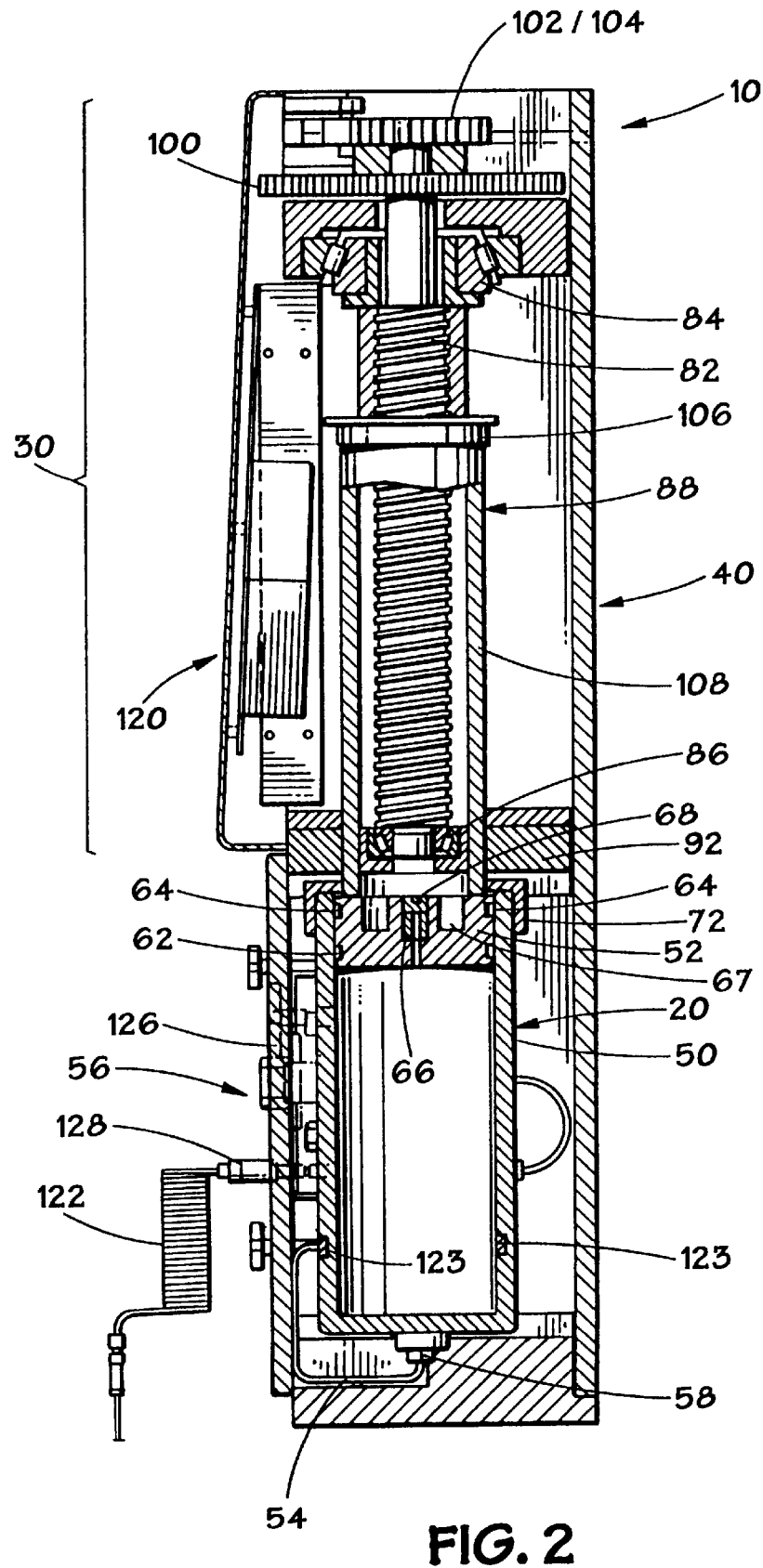
FIG. 2 is a partial cross-sectional side view of the high pressure infusion system of FIG. 1.

As shown in FIGS. 1 and 2, high pressure fluid delivery system 10 of the present invention generally comprises fluid assembly 20 for generating and holding a fluid to be gas-supersaturated and delivered, and drive assembly 30 for delivering the gas-supersaturated fluid from the fluid assembly at a high delivery pressure. Fluid and drive assemblies 20, 30 are mounted in housing 40 with fluid assembly 20 being removable as explained below.

Figure 3:
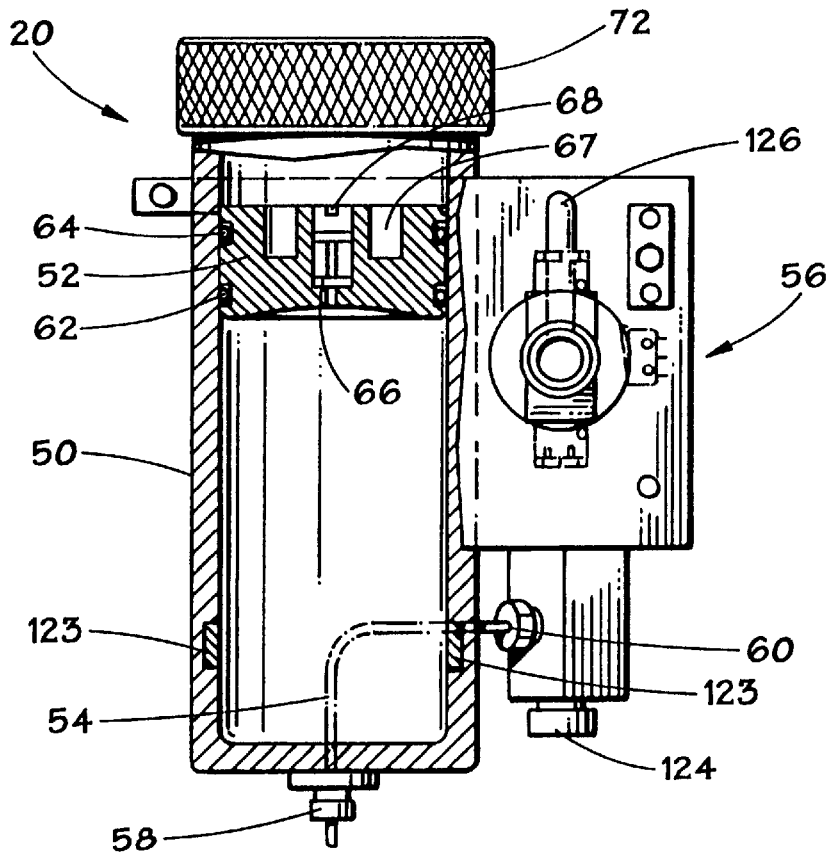
FIG. 3 is a partial cross-sectional front view of a fluid assembly of the high pressure infusion system of FIG. 1.
Figure 4:
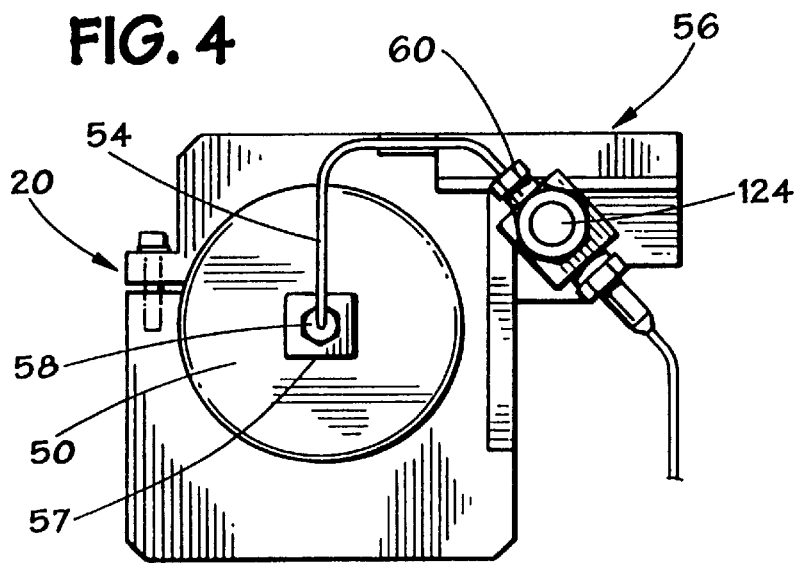
FIG. 4 is a bottom view of the fluid assembly of FIG. 3.
Figure 5:
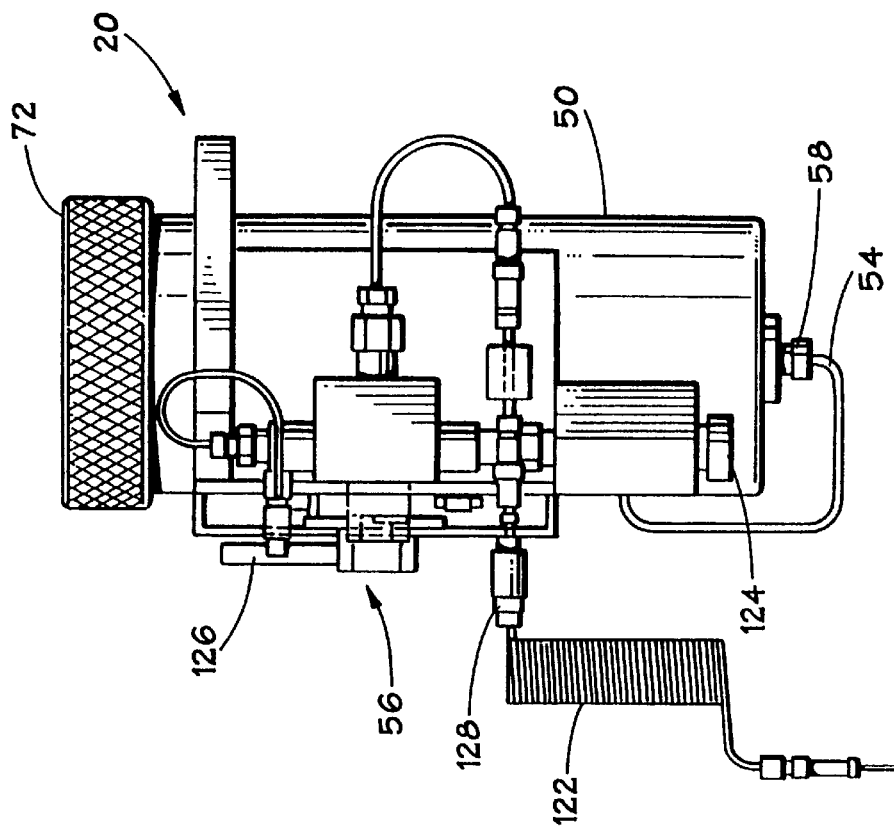
FIG. 5 is a side view of the fluid assembly of FIG. 3.

As best shown in FIGS. 3–5, fluid assembly 20 comprises cylinder 50, piston 52, cylinder output fitting 58, housing output tubing 54 and output manifold 56. Housing output tubing 54 connects fitting 58 to manifold input port 60. Manifold 56 monitors the hydrostatic pressure of the fluid in cylinder 50. Cylinder 50 is preferably made of a corrosion resistant and strong material, such as titanium. In order to ensure smooth travel of piston 52 within cylinder 50, the interior surface of cylinder 50 is preferably smooth.

Piston 52, as shown in FIGS. 1, 2 and 3, comprises high pressure seal 62, guide ring 64, fluid and gas introduction barrier 66 and port 68. High pressure seal 62 prevents undesired escape of gas and/or fluid from the cylinder. High pressure seal 62 is preferably U-shaped such that seal 62 is at least partially forced against the inner surface of cylinder 50 by the pressure of the gas and/or fluid within cylinder 50. Thus, an increase in the pressure of the gas and/or fluid within cylinder 50 increases the sealing force exerted by seal 62 against the inner surface of cylinder 50 and thereby resulting in a stronger seal.

A trocar or other suitable cannula is inserted into port 68 for the introduction of fluid and gas into cylinder 50 through introduction barrier 66. Introduction barrier 66 is preferably a manually operated ball valve such that a seal is maintained after the cannula is removed from port 68, especially for hydrostatic pressures approximately 500 psi or higher. See FIG. 7. Alternatively, for hydrostatic pressures approximately 500 psi or less, introduction barrier 66 may be made of a medical grade silicon rubber (not shown in FIG. 7; see FIGS. 1–3) such that a seal is maintained when pierced by the cannula during the introduction of fluid and gas into cylinder 50.

Piston 52 may also provide threaded annular recess 67. Threaded annular recess 67 allows for attachment of a piston handle (not shown) to facilitate movement of piston away from fitting 58 and to facilitate removal of piston 52 from cylinder 50, especially when the contents of the cylinder are not pressurized. Removal of piston 52 may desirable, for example, to clean interior surfaces of cylinder 50.

Figure 7:
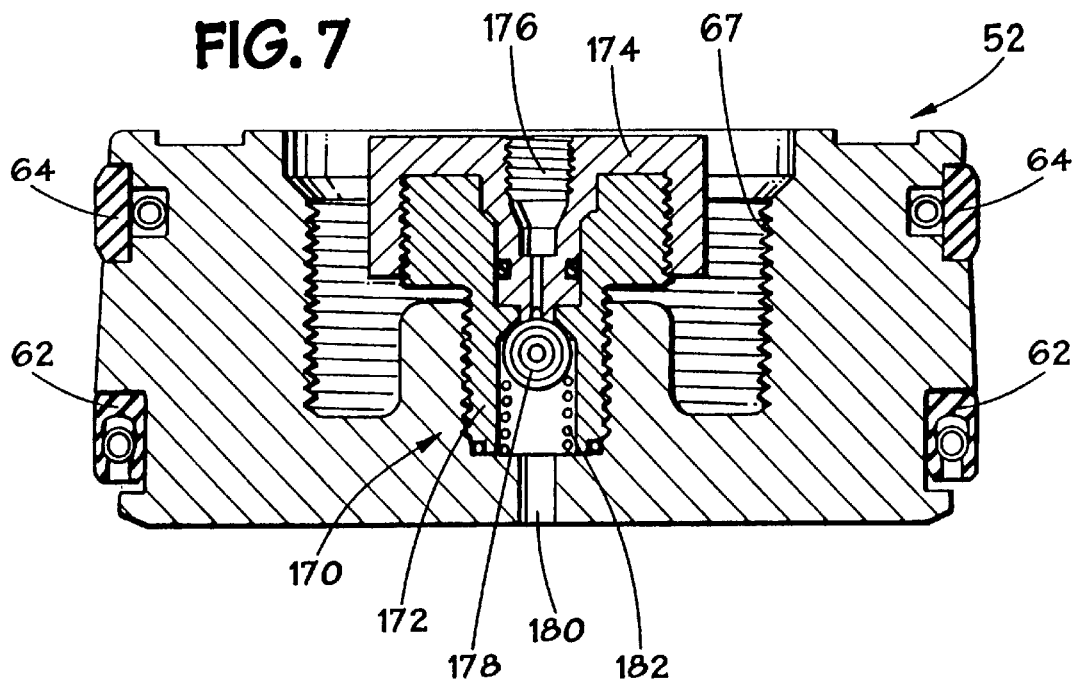
FIG. 7 is a cross-sectional view of an alternate exemplary piston assembly of the high pressure infusion system of the present invention.

An alternate exemplary piston assembly 55 is shown in FIG. 7. The piston assembly 55 advantageously comprises a ball valve assembly 170 including a valve seat assembly 172 in threaded sealed engagement with the piston 52 and with the ball valve actuator 174. A fluid pathway extends through the ball valve actuator 174 between the fluid inlet port 176 and the end of the fluid pathway proximate the ball 178. When the actuator 174 is rotated to move toward the fluid outlet 180, a portion of the actuator 174 presses against and moves the ball 178 downward against the action of spring 182. In this first position, fluid provided via fluid inlet port 176 may be introduced through the piston 52, e.g., to fill the fluid receptacle of a fluid assembly. When the actuator 174 is rotated to move away from the fluid outlet 180, the actuator loses contact with the ball 178. In this second position, the ball 178 seats against a portion of the valve seat assembly 172 as a result of the action of the spring 182 and any pressure within the fluid receptacle of the fluid assembly. Thus, for example, any fluid under pressure within the receptacle cannot escape through the valve assembly 170, however any fluid supplied to fluid inlet port 176 at a pressure greater than the pressure of the ball 178 against its seat may be introduced into the receptacle.

Figure 6:
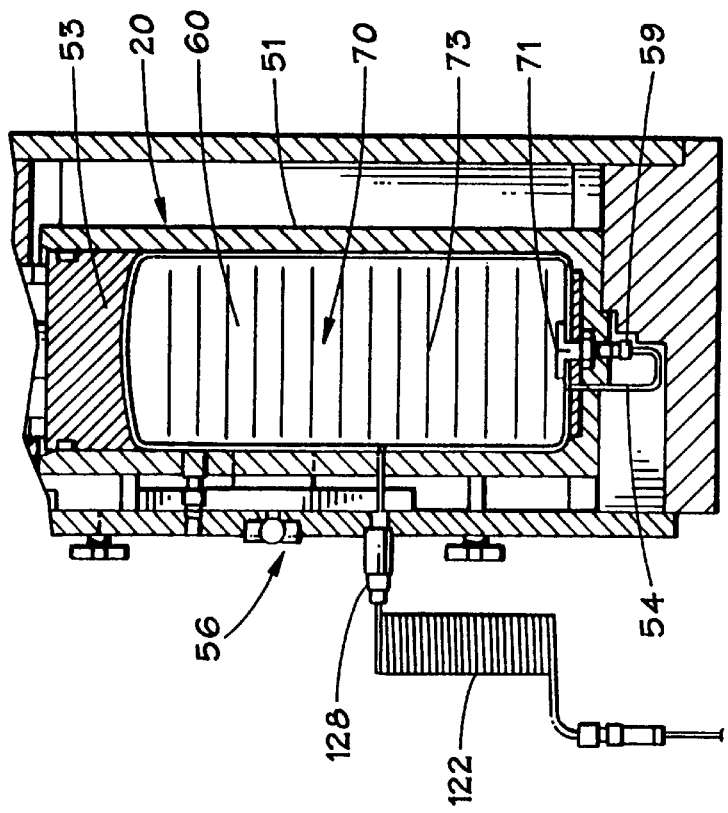
FIG. 6 is a partial cross-sectional side view of a portion of a high pressure infusion system with an alternative embodiment of a fluid assembly.

In an alternative embodiment, as shown in FIG. 6, fluid assembly 20 also includes disposable and replaceable fluid container 70 within cylinder 51. Preferably, cylinder 51 is hinged along a curved surface for ease of inserting disposable container 70 into and removing disposable container 70 out of cylinder 51. Disposable container 70 provides output port 71 for attachment to fitting 59 for the delivery of fluid from disposable fluid container 70.

Disposable container 70 may be tubular and made of a flexible and collapsible material, and when properly supported, capable of withstanding pressures of 5,000 psi or greater. As shown in FIG. 6, disposable container 70 may also be provided with preset fold lines 73 such that when piston 53 advances toward fitting 59 and compresses disposable container 70, disposable container 70 collapses in a predetermined manner and thereby minimizes risks of rupture. Flexible disposable fluid container 70 may further provide an input port (not visible in FIG. 6) for attachment to a port for the introduction of fluid and gas into disposable container 70.

Alternatively, disposable container 70 may be made of a rigid plastic such that disposable container 70 does not fold or collapse within cylinder 51. One end of rigid disposable container 70 proximate to a piston is open and thereby eliminating the need for an input port. The open piston end of rigid disposable container 70 allows the piston to travel along the inner surface of rigid container 70.

Although the following description describes system 10 with flexible and collapsible disposable fluid container 70, one of ordinary skill in the art can easily adapt and apply the following description to system 10 with the use of rigid disposable container 70 or without the use of disposable fluid container 70.

In order to generate a gas-supersaturated fluid, fluid assembly 20 is removed from delivery system housing 40. Disposable container 70 is inserted into cylinder 51 such that the input port of container 70 is connected to a fluid inlet port. To fill disposable container 70 with a fluid, for example physiologic saline or lactated ringers solution, a cannula connected to a fluid source, such as a syringe, is inserted through an introduction barrier and the fluid is introduced into disposable container 70 via the port.

In this exemplary embodiment, the volume of cylinder 51 and the maximum volume of disposable container 70 is approximately 1.1 liters. Preferably, fluid is introduced until disposable container 70 fills cylinder 51 and is completely filled with the fluid. A small known volume of fluid, for example 0.1 liter, is removed from disposable container 70 through the cannula resulting in the same known volume of air above the fluid within disposable container 70. Thus, the volumes of fluid and air within disposable container 70 are known. In this exemplary embodiment, disposable container 70 contains approximately 1.0 liter of fluid and 0.1 liter of air.

To gas-supersaturate the fluid in disposable container 70, fluid assembly 20 is inverted such that piston 53 is below fitting 59 and at an end of cylinder 51 opposite fitting 58. A gas source is connected to the cannula in place of or in combination with the fluid source. The gas, such as oxygen, is introduced into disposable container 70 via the fluid inlet port at a pressure that is the same or slightly above the desired resultant partial pressure of the gas.

As gas bubbles flow upward through the fluid in disposable container 70, the gas is dissolved into the fluid and also displaces other previously dissolved gases in the fluid. Excess undissolved gas exits disposable fluid container 70 and cylinder 51 through fitting 59. Because of the relatively quick diffusion process due to the relatively large surface area of the gas bubbles, the process of gas-supersaturating the fluid can be completed in a short period of time. For example, with a gas flow of 5–10 standard $ft^3/hr$ in a 1.1 liter cylinder, the fluid can be gas-supersaturated in approximately 1 hour.

After gas-supersaturating the fluid to the desired gas partial pressure, the cannula is removed from the introduction barrier. A piston cap (see, e.g., piston cap 72 of FIGS. 1–2) may be attached onto cylinder 51 over piston 53. Because the contents of fluid container 70 are under pressure, the piston cap facilitates in retaining piston 53 completely within cylinder 51 prior to returning fluid assembly 20 to delivery system housing 40. The piston cap may define an annular lip for retaining piston 53 further within cylinder 51.

Figure 11:
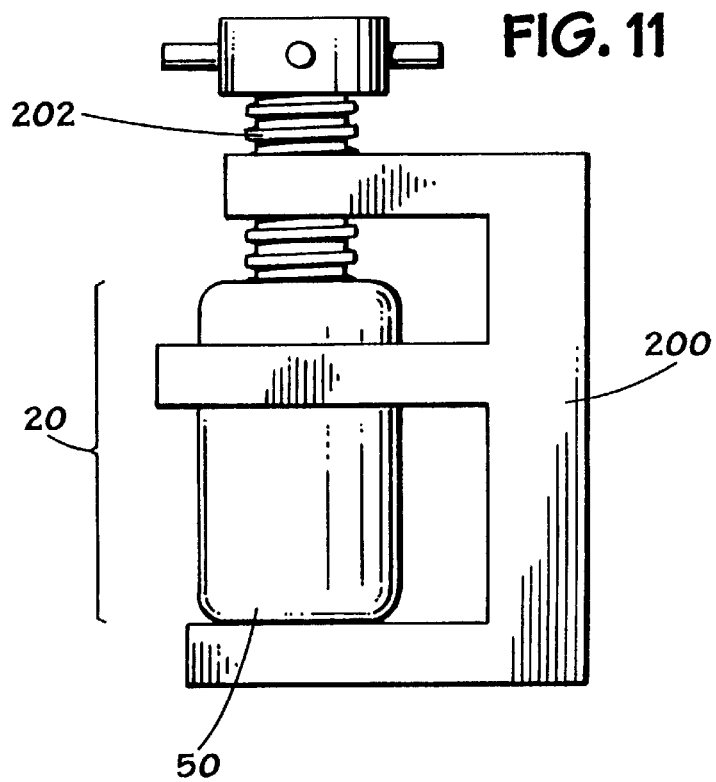
FIG. 11 is a schematic diagram of a separate support and jack used in fluid processing according to one embodiment.

A support structure 200 (FIG. 11) for holding fluid assembly 20 may be utilized such that piston 53 can be advanced with, for example, jack 202. A variety of arrangements other than that shown schematically in FIG. 11 may be devised for this purpose. A valve is opened and piston 53 is advanced upward toward fitting 58 just until fluid begins to exit through the valve. Thus, the volume of gas above the fluid within disposable container 70 has been eliminated. The valve is preferably a two-way valve, especially for high gas partial pressures. At lower gas partial pressures (about 15 psi), fitting 58 may be disconnected and a separate valve assembly may be connected to cylinder 51. After the volume of gas is removed, additional fluid is then added into disposable container 70, for example, with a high pressure syringe, to increase the hydrostatic pressure above the desired gas partial pressure. As an example with the system described above, pressure may be increased from 500 psi to 750–1000 psi. Alternatively, the high pressure syringe may be used instead of jack 202 to eliminate the gas space in the cylinder while maintaining the pressure. The valve is then closed to prevent further escape of fluid or gas through the valve.

It may be desirable to store the gas-supersaturated fluid in disposable container 70 under an increased hydrostatic pressure in order to dissolve or minimize the size of any bubble nuclei in the fluid and in order to store the fluid for a period of time until the fluid is to be delivered. To increase the hydrostatic pressure of the fluid within disposable container 70, piston 53 can be advanced further. For example, piston 53 may be advanced until the hydrostatic pressure is increased a significant amount over the gas partial pressure. Increasing the hydrostatic pressure also helps to prevent the hydrostatic pressure from dropping below the gas partial pressure as a result of, for example, a decrease in the temperature of the fluid and therefore also helps prevent bubble nucleation.

For gas partial pressures of approximately 50 psi or less, because fluid assembly 20 can be removed from the support structure 200 and loaded into delivery system housing 40 in a relatively short period of time, for immediate delivery of the gas-supersaturated fluid, use of piston cap 72 may not be necessary. At such gas partial pressures, even without the use of piston cap 72, few bubble nuclei, if any, would form as bubble nuclei require a relatively longer period of time to form and any decrease in the hydrostatic pressure as a result of not using piston cap 72 to retain piston 52 completely within cylinder 51 would be relatively small.

After gas-supersaturating the fluid, fluid assembly 20 is removed from the support structure 200 and returned to delivery system housing 40. Fluid assembly 20 is oriented within system housing 40 such that piston 53 is above fitting 58 and coupled to drive assembly 30 for high pressure delivery of the gas-supersaturated fluid to a desired site.

As shown in FIGS. 1–2 and 8–9, drive assembly 30 generally comprises drive system 80 for driving ball screw 82; main bearing 84 and support bearing 86 for engaging with ball screw 82; piston pusher 88 driven by ball screw 82 for advancing piston 52 toward fitting 58; travel limit switches 90 for ensuring that piston pusher travel is within predetermined limits; and piston pusher anti-rotation plate 92 for preventing ball screw 82 from rotating piston pusher 88.

Figure 8:
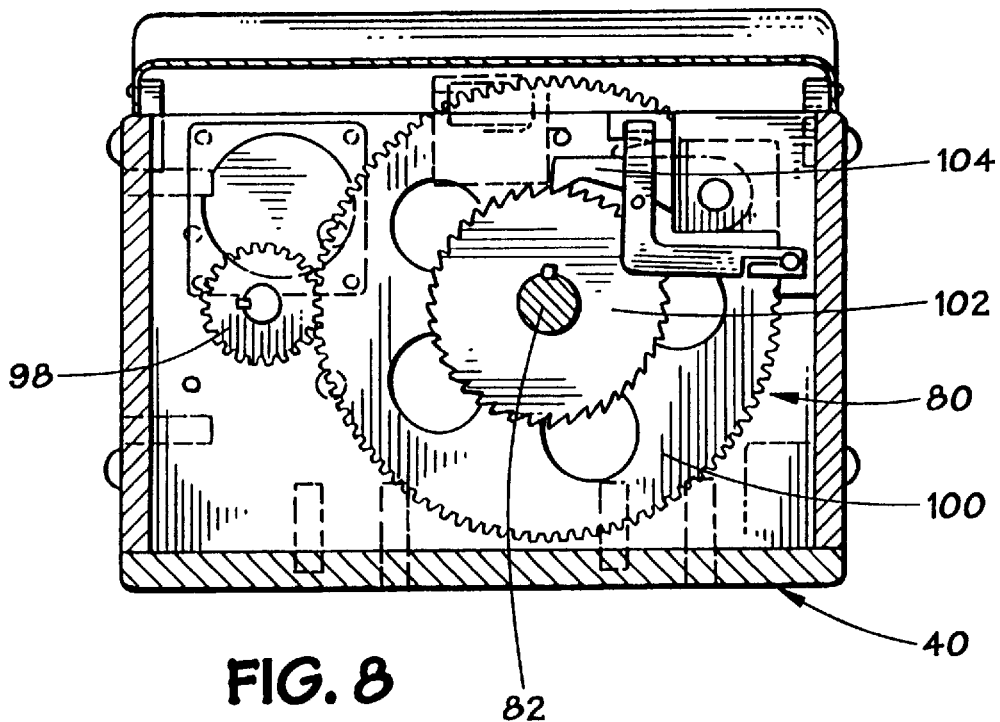
FIG. 8 is a cross-sectional top view of the high pressure infusion system of FIG. 1 showing a drive system.

Drive system 80 as shown in FIGS. 1 and 8 comprises stepper motor 94 for driving high torque gear box 96 (with a gear ratio of, for example, 112:1) which drives drive gear 98 (with a gear ratio of, for example, 4:1). Drive gear 98 in turn drives main gear 100, fixably attached to ball screw 82 and ratchet wheel 102 and pawl 104. When pawl 104 engages ratchet wheel 102, pawl 104 prevents main gear 100 and piston pusher 88 from rotating in an undesired direction, even if power to system 10 is terminated. Thus, ratchet wheel 102 and pawl 104, when engaged, prevent piston pusher 88 and piston 52 from traveling upward and away from fitting 58.

As shown in FIGS. 1–2, main and support bearings 84, 86 each engage and support an end of ball screw 82 near drive system 80 and near piston pusher anti-rotation plate 92, respectively. Main bearing 84 and support bearing 86 help to minimize frictional loading from direct load forces and from side load forces due to possible imperfect alignment of ball screw 82 and/or piston 52. Main bearing 84 and support bearing 86 also ensure concentric rotation of ball screw 82 even under high loads from the high pressures within cylinder 50. Having a two bearing arrangement provides superior alignment and support which allows high pressure fluid delivery to be achieved and accurately controlled without an oversized or bulky apparatus.

Piston pusher 88 comprises upper engagement portion 106 and lower split portion 108. Engagement portion 106 is annular with a threaded interior for coupling with ball screw 82 such that rotation of ball screw 82 advances piston pusher 88 either toward or away from fitting 58 depending on the direction of ball screw rotation. The use of ball screw 82 to advance piston pusher 88 also provides an accurate measure of the fluid delivery rate and the total fluid volume delivered.

Engagement portion 106 of piston pusher 88 includes flange 110 which acts as a travel limit switch activator such that functions of drive assembly 30 are terminated when flange 110 makes contact with either of two travel limit switches 90, thereby ensuring that piston pusher travel is within the predetermined limits.

Figure 9:
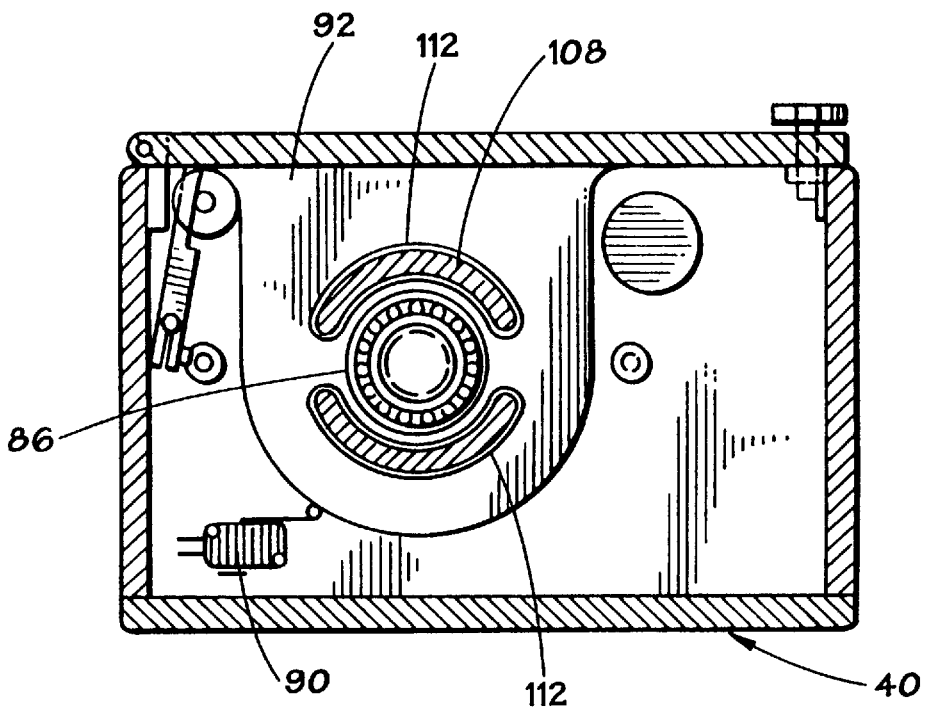
FIG. 9 is a cross-sectional top view of the high pressure infusion system of FIG. 1 showing a main bearing and a piston pusher, and a piston pusher anti-rotation plate.

As shown in cross-sectional view in FIG. 9, split portion 108 of piston pusher 88 comprises two semi-circular sections to allow piston pusher 88 to travel past support bearing 86, anti-rotation plate 92 and piston cap 72. Piston pusher anti-rotation plate 92 is fixably attached to delivery system housing 40 and provides one or more apertures 112, through which the two semi-circular sections of split portion 108 may travel. Piston pusher anti-rotation plate 92 prevents rotation of piston pusher 88 such that rotation of ball screw 82 advances piston pusher 88 either toward or away from fitting 58 depending on the direction of ball screw rotation. Piston pusher anti-rotation plate 92 may also support support bearing 86. Piston cap 72 similarly provides one or more apertures for allowing piston pusher 88 to travel past piston cap 72.

Figure 10:
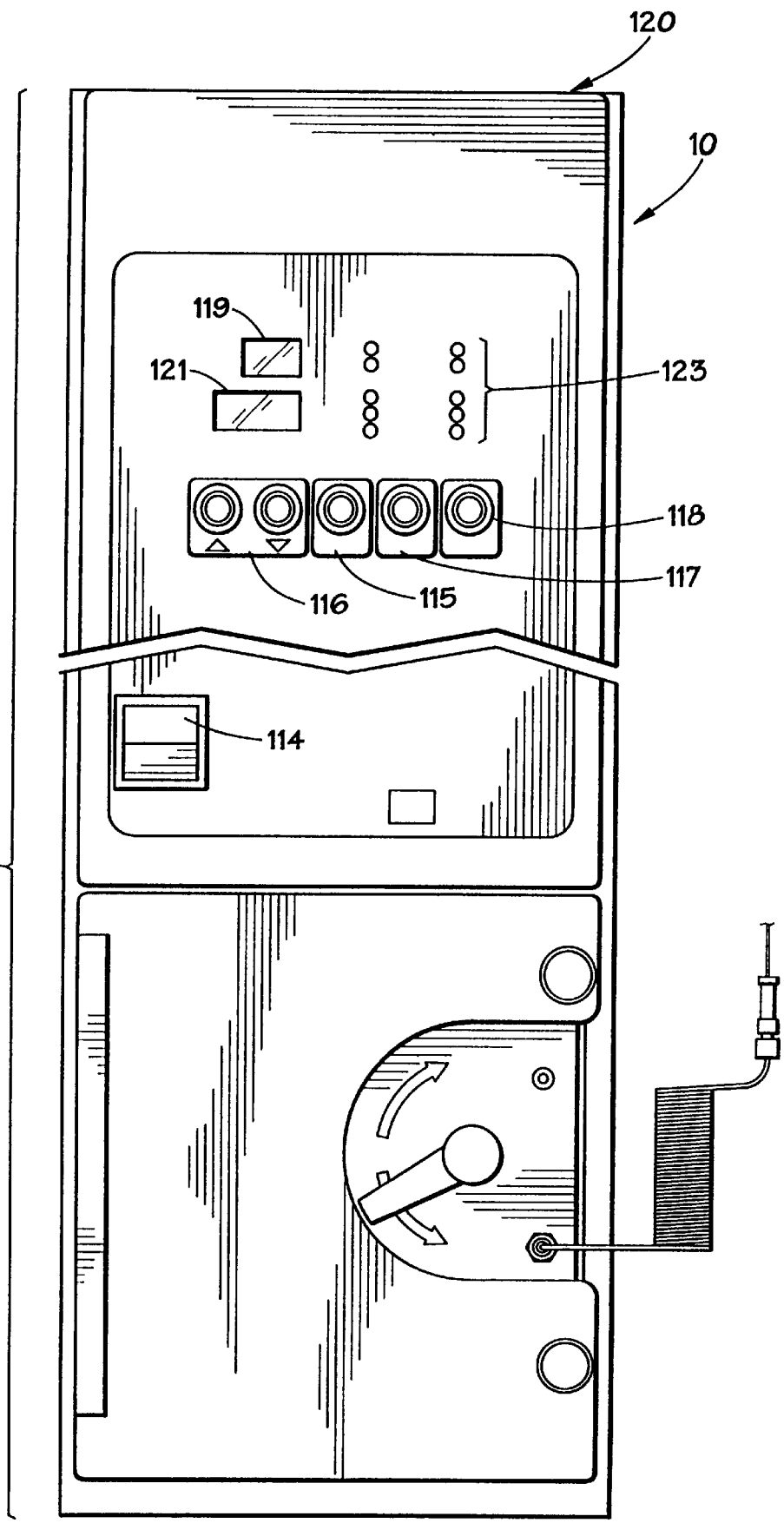
FIG. 10 is a front view of the high pressure infusion system of FIG. 1 showing a user interface.

As shown in FIG. 10, to facilitate operation of system 10, a user interface is provided on front panel 120 of delivery system housing 40 for allowing a user to specify and control operating parameters and indicating to the user certain operating parameters. The user interface may include power switch 114 for supplying and cutting off power to system 10; LOAD button 115 for fluid delivery preparation by advancing piston pusher 88 until the hydrostatic pressure approximately equals the desired delivery pressure; a FLOW switch 116 for increasing and decreasing the fluid delivery rate; a RATCHET switch (not shown) for engaging and disengaging pawl 104 from ratchet wheel 102 to prevent or allow rotation of ball screw 82 in a direction that advances piston pusher 88 upward and away from fluid assembly 20; UNLOAD button 117 for advancing piston pusher 88 upward after disengaging pawl 104 from ratchet wheel 102; and an ALARM ACKNOWLEDGE 118 button to allow the user to acknowledge an indicated error and continue fluid delivery.

The user interface may further provide displays 119, 121 to indicate the specified delivery rate (e.g. 10.5 cc/min) and the total volume delivered (e.g. 275 cc). The user interface may also provide various lights 123 to indicate certain operating conditions of system 10.

To prepare system 10 for delivery of the gas-supersaturate fluid in fluid assembly 20, the user inputs the necessary operating parameters such as the fluid delivery rate, total fluid delivery volume, and fluid delivery pressure. The user then depresses LOAD button 115 on the user interface. By pressing LOAD button 115, piston pusher 88 advances piston 52 toward fitting 58 until the hydrostatic pressure of the fluid within disposable container 70 reaches the desired delivery pressure. Such further pressurization of the fluid also serves as a final compression and stabilization of the gas-supersaturated fluid within disposable container 70. The desired delivery pressure is dependent upon the desired fluid delivery rate and the size of system fluid delivery device 122 used for fluid delivery to the desired site. Lights 123 may provide an indicator for indicating when the hydrostatic pressure has reached the desired delivery pressure.

To monitor the temperature of the fluid in cylinder 50, system 10 may provide a pair of thermistors 123 located in the interior cylindrical wall of cylinder 50. The pair of thermistors provides redundancy in order to ensure reliable and accurate monitoring of the temperature of the fluid. System 10 may further provide a heater jacket (not shown) encircling cylinder 50 to control the temperature of the fluid therein. With a pair of redundant thermistors and a heater jacket to control the temperature, system 10 provides accurate and reliable control and monitoring of the temperature of the fluid in cylinder 50. This may be especially desirable, for example, when a significant fluid flow, for example 10–50 cc/min, is delivered to a patient's coronary arteries.

System 10 may further comprise a flow meter to monitor the output flow velocity of the fluid from cylinder 50. To monitor the hydrostatic pressure of the fluid from cylinder 50, manifold 56 comprises a fluid pressure sensor. In order to prevent fluid delivery at an excessively high delivery pressure, manifold 56 may further comprise rupture disc 124 in fluid communication with the fluid to be delivered. When the fluid delivery pressure exceeds the maximum pressure rupture disc 124 withstand, rupture disc 124 ruptures. After rupture disc 124 ruptures, fluid flow to system fluid delivery device 122 for fluid delivery to the desired site terminates and fluid flow is redirected away from system 10.

Fluid flows out of cylinder 50 through housing output tubing 54 and into manifold 56. As shown in FIGS. 3 and 5, fluid flows out of manifold 56 via two-way flow/flush valve 126 of manifold 56. When open, two-way flow-flush valve 126 allows delivery of either the gas-supersaturated fluid or a flush fluid (such as saline) to the desired delivery site at a low fluid delivery rate. Such low delivery of a flush fluid allows a continuous fluid flow to the fluid delivery site. For example, when system 10 is utilized to deliver gas-supersaturated fluids to a patient, even when fluid delivery at the specified delivery rate is no longer necessary or desired, maintaining a continuous fluid flow may be desirable to prevent coagulation problems.

Output fluid filter 128 may be provided to filter fluid flowing from two-way valve 126. Fluid is then delivered from output fluid filter 128 to the delivery site via system fluid delivery device 122. For example, for delivery of the gas-supersaturated fluid to a patient, system fluid delivery device 122 may be an infusion device comprising a 400 cm flex spiral tubing connected to a guidewire.

The present invention has been described in terms of exemplary embodiments. The invention, however, is not limited to the embodiments depicted and described. Rather, the scope of the invention is defined by the appended claims.

What is claimed is:

1. An apparatus for preparing and delivering a gas-supersaturated fluid to a delivery site, comprising:
    a fluid assembly comprising a cylinder, the cylinder having one or more ports for input and output of fluid and gas; a fluid container positionable within the cylinder and removable therefrom, the fluid container being adapted for containing the fluid and gas and having one or more ports in fluid and gaseous communication with the one or more ports of the cylinder; and a piston adapted to travel within the cylinder and to pressurize the contents of the fluid container and to deliver the gas-supersaturated fluid at predetermined fluid delivery pressures;
    a drive assembly comprising a piston pusher for advancing the piston within the cylinder and a drive system for advancing the piston pusher;
    a system housing for housing the fluid assembly and the drive assembly, the fluid assembly being removable from the system housing.

2. The apparatus of claim 1, wherein the fluid container is adapted to be compressible by the piston as it advances.

3. The apparatus of claim 2, wherein the fluid container is configured to have a plurality of fold lines and being adapted to collapse in a predetermined manner as the piston advances.

4. The apparatus of claim 3, wherein the fluid container is plastic.

5. The apparatus of claim 4, wherein the fluid container is disposable.

6. The apparatus of claim 1, wherein the fluid container is made of a rigid material and the piston is adapted to travel within the fluid container.

7. The apparatus of claim 1, wherein the drive assembly further comprises a ball screw rotated by the drive system, wherein rotation of the ball screw in a first direction advances the piston pusher toward the fluid assembly and rotation in a second direction advances the piston pusher away from the fluid assembly.

8. The apparatus according to claim 7, wherein the drive assembly further comprises a first bearing and a second bearing supporting the ball screw wherein the first bearing is located near an end of the ball screw between the piston pusher and the drive system and the second bearing is located at an opposite end of the ball screw.

9. The apparatus according to claim 8, wherein the piston pusher comprises an engagement portion which engages the ball screw and a split portion which contacts the piston to advance the piston, the split portion comprising at least two sections extending from the engagement portion to allow the split portion of the piston pusher to travel past the second bearing.

10. The apparatus according to claim 9, wherein the drive assembly further comprises a piston pusher anti-rotation plate fixably attached to the system housing, the anti-rotation plate having at least two apertures adapted for receiving the at least two sections of the split portion of the piston pusher, wherein the anti-rotation plate prevents rotation of the piston pusher such that rotation of ball screw advances the piston pusher.

11. The apparatus according to claim 1, wherein the fluid assembly includes a manifold which comprises a flow-flush valve in fluid communication with the cylinder port and having an output for connection to a system delivery apparatus for delivering the fluid to the delivery site, the valve having a first position for providing fluid flow from the cylinder to the delivery site, a second position for providing a low-velocity flow of a flush fluid from a flush fluid source and a closed position for preventing fluid flow from the system.

12. The apparatus according to claim 11, wherein the manifold includes a rupture disc in fluid communication with the cylinder port, the rupture disc adapted to rupture when fluid pressure of the fluid exceeds a predetermined safety pressure thereby terminating fluid flow from the system.

13. An apparatus for preparing and delivering a gas-supersaturated fluid, comprising:

a power screw having first and second ends supported by bearings;

a piston pusher traveling on the power screw in response to rotation thereof, said piston pusher comprising a collar portion engaging the power screw and at least two depending portions extending from the collar portion along the power screw;

a support plate adjacent one end of the power screw to support a bearing and said one end of the power screw, said support plate defining at least to apertures to permit said depending portions of the piston pusher to pass therethrough;

a cylinder disposed on an opposite side of the support plate from the power screw;

a fluid container positionable within the cylinder and removable therefrom; and a piston sealingly and slidably received in the cylinder and acted on by the depending portions of the piston pusher to exert pressure on the fluid container.

14. The apparatus according to claim 13, wherein said power screw and support plate are mounted in a housing and said piston and cylinder are removably receivable in said housing to be acted on by said piston pusher.

15. An apparatus for preparing and delivering a gas-supersaturated fluid, comprising:

a support structure;

a drive mechanism supported by the support structure for advancing a piston pusher; and a fluid assembly mounted on the support structure and adapted to be removable therefrom comprising a cylinder, the cylinder having one or more ports for input and output of fluid and gas; a fluid container adapted to be positionable within the cylinder and removeable therefrom, the fluid container having one or more ports in fluid and gaseous communication with the one or more ports of the cylinder; and a piston disposed within the cylinder and adapted to travel within the cylinder in cooperation with the piston pusher for advancement of the piston, the piston also is adapted to exert pressure on the fluid container and to deliver gas-supersaturated fluid at a predetermined fluid delivery pressure.

16. The apparatus of claim 15, wherein the fluid container is adapted to be compressible by the piston as it advances.

17. The apparatus of claim 16, wherein the fluid container is configured to have a plurality of fold lines and being adapted to collapse in a predetermined manner as the piston advances.

18. The apparatus of claim 17, wherein the fluid container is plastic.

19. The apparatus of claim 18, wherein the fluid container is disposable.

20. The apparatus of claim 15, wherein the fluid container is made of a rigid material and wherein the piston is adapted to travel within the fluid container.

21. The apparatus of claim 15, wherein the drive mechanism comprises a screw for advancing the piston pusher, the screw having two ends, each end supported by a bearing.

22. The apparatus of claim 21, wherein the piston pusher comprises a coupling for engaging with the screw and a split portion comprising at least two sections disposed around one of the bearings such that the pusher may pass beyond the bearing, the split portion engaging with the piston.

23. The apparatus of claim 22, further comprising a split portion plate comprising at least two orifices adapted to receive the at least two sections of the split portion for preventing rotation of the piston pusher.

24. The apparatus according to claim 15, wherein the cylinder further comprises at least one thermistor for monitoring temperature of fluid and gas in the cylinder.

25. The apparatus according to claim 15, wherein the cylinder further comprises at least one pressure gauge in fluid and gaseous communication with fluid and gas in the cylinder for monitoring pressure of the fluid and gas in the cylinder.

26. A method for preparing and delivering a gas-supersaturated fluid to a delivery site, comprising the steps of:

providing a fluid assembly comprising a cylinder, the cylinder having one or more ports for input and output of fluid and gas; a fluid container positionable within the cylinder and removable therefrom, the fluid container being adapted for containing the fluid and gas and having one or more ports in fluid and gaseous communication with the one or more ports of the cylinder; and a piston adapted to travel within the cylinder;

filling the fluid container with a fluid and introducing a gas under pressure to thereby gas-supersaturate the fluid;

placing the fluid assembly in a system housing containing a drive mechanism assembly, the drive mechanism comprising a piston pusher adapted to advance the piston within the cylinder and to compress the fluid container;

advancing the piston pusher until hydrostatic pressure of the gas-supersaturated fluid in the fluid container is at a desired predetermined delivery pressure;

selecting a flow position of a flow-flush valve for delivery of the gas-supersaturated fluid from the system to the delivery site, the valve being in fluid communication with one of the cylinder ports; and advancing the piston pusher at a predetermined rate to deliver the gas-supersaturated fluid at the desired predetermined delivery pressure.

27. The method of claim 26, wherein the fluid container is adapted to be compressible by the piston as it advances.

28. The method of claim 27, wherein the fluid container is configured to have a plurality of fold lines and being adapted to collapse in a predetermined manner as the piston advances.

29. The method of claim 28, wherein the fluid container is plastic.

30. The method according to claim 29, wherein the fluid container is disposable.

31. The method of claim 26, wherein the fluid container is made of a rigid material and wherein the piston is adapted to travel within the fluid container.

32. A method for delivering a gas-supersaturated fluid to a delivery site, comprising the steps of:

providing a fluid assembly comprising a cylinder having one or more ports for input and output of fluid and gas; a fluid container positionable within the cylinder and removable therefrom, the fluid container containing the gas-supersaturated fluid and having one or more ports in fluid and gaseous communication with the one or more ports of the cylinder, and a piston adapted to travel within the cylinder and to pressurize the gas-supersaturated fluid in the fluid container and to deliver the gas-supersaturated fluid at predetermined fluid delivery pressures;

placing the fluid assembly in a system housing containing a drive mechanism assembly, the drive mechanism comprising a piston pusher adapted to advance the piston within the cylinder;

advancing the piston pusher until the hydrostatic pressure of the gas-supersaturated fluid in the fluid container is at a desired predetermined delivery pressure;

selecting a flow position of a flow-flush valve for delivery of the gas-supersaturated fluid from the system to the delivery site, the valve being in fluid communication with one of the cylinder ports; and advancing the piston pusher at a predetermined rate to deliver the gas-supersaturated fluid at the desired predetermined delivery pressure.

33. The method of claim 32, wherein the fluid container is adapted to be compressible by the piston as it advances.

34. The method of claim 33, wherein the fluid container is configured to have a plurality of fold lines and being adapted to collapse in a predetermined manner as the piston advances.

35. The method of claim 34, wherein the fluid container is plastic.

36. The method according to claim 35, wherein the fluid container is disposable.

37. The method of claim 32, wherein the fluid container is made of a rigid material and wherein the piston is adapted to travel within the fluid container.

* * * * *